(12) United States Patent
Minamino (10) Patent No.: US 11,007,172 B2
(45) Date of Patent: May 18, 2021

(54) AGENT FOR ELIMINATING SENESCENT CELLS

(71) Applicants: NIIGATA UNIVERSITY, Niigata (JP); MITSUBISHI TANABE PHARMA CORPORATION, Osaka (JP)

(72) Inventor: Tohru Minamino, Niigata (JP)

(73) Assignees: NIIGATA UNIVERSITY, Niigata (JP); MITSUBISHI TANABE PHARMA CORPORATION, Osaka (JP)

( * ) Notice: Subject to any disclaimer, the term of this patent is extended or adjusted under 35 U.S.C. 154(b) by 0 days.

(21) Appl. No.: 16/329,154

(22) PCT Filed: Aug. 29, 2017

(86) PCT No.: PCT/JP2017/030867
§ 371 (c)(1),
(2) Date: Feb. 27, 2019

(87) PCT Pub. No.: WO2018/043463
PCT Pub. Date: Mar. 8, 2018

(65) Prior Publication Data
US 2019/0192482 A1 Jun. 27, 2019

(30) Foreign Application Priority Data
Aug. 30, 2016 (JP) .............................. JP2016-167679

(51) Int. Cl.
| | | |
|---|---|---|
| A61K 31/351 | (2006.01) | |
| A61K 31/7042 | (2006.01) | |
| A61K 31/381 | (2006.01) | |
| A61K 45/00 | (2006.01) | |
| A61P 43/00 | (2006.01) | |
| A61P 7/02 | (2006.01) | |

(52) U.S. Cl.
CPC ............ *A61K 31/381* (2013.01); *A61K 45/00* (2013.01); *A61P 7/02* (2018.01); *A61P 43/00* (2018.01)

(58) Field of Classification Search
CPC .......................... A61K 31/351; A61K 31/7042
USPC ............................................. 514/23, 27, 32
See application file for complete search history.

(56) References Cited

U.S. PATENT DOCUMENTS 9,198,925 B2 * 12/2015 Bindra ...................... A61K 9/16
2014/0303097 A1 * 10/2014 Broedl ............... A61K 31/7048
514/23

OTHER PUBLICATIONS

Written Opinion of the International Searching Authority for PCT/JP2017/030867 (PCT/ISA/237) dated Nov. 14, 2017, with English translation.
Hiratsuka et al., "Jicchi Ika no Tameno Kokarei Igaku no Rinsho Seminor Shinpo shita Anti-aging no Kiso to sono Jicchi Chiryo eno Katsuyo no Jissai Tonyobyo to Anti-aging", Medical Practice, 2014, vol. 31, No. 7, ISSN: 0910-1551, total of 5 pages.
Imamura, "Kaisetsu SGLT2 Sogaiyaku no Shiyoho", The Journal of Japan Physicians Association Kaishi, Mar. 2016, vol. 30, No. 5, ISSN: 0914-9627, total of 8 pages.
International Search Report for PCT/JP2017/030867 (PCT/ISA/210) dated Nov. 14, 2017.
Minamino et al., "A crucial role for adipose tissue p53 in the regulation of insulin resistance", Nature Medicine, vol. 15, No. 9, Sep. 2009, total of 8 pages.
Obata et al., Tokushu 2-gata Tonyobyo no Atarashii Chiryo Senryaku: Shinki Tonyobyo Chiryoyaku o do Katsuyo suru? I. SGLT2 Sogaiyaku no Tonyobyo Chiryo ni Okeru Senryakuteki Ichizuke Tekishita Kanjazo, Tekisanai Kanjazo, Diabetes, 2015, vol. 7, No. 6, total of 11 pages.
Ogiwara et al., "Roka Sokushin Model Mouse Jinzo ni Okeru Toyusotai no Hen'i to No Kino Teika", Abstracts of 131st Annual Meeting of Pharmaceutical Society of Japan 3, 2011, ISSN: 0918-9823, total of 3 pages.
Takase et al., "Kandomyaku Shikkan o Gappei shita Tonyobyo Shorei ni Okeru SGLT2 Sogaiyaku no Kekkan Naihi Kino ni Oyobosu Eikyo; Preliminary Study", Dai 30 Kai Journal of The Japanese Coronary Association, Nov. 24, 2016, ISSN: 1341-7703, total of 2 pages.
Bonomini et al. "Metabolic Syndrome, Aging and Involvement of Oxidative Stress," Aging and Disease, Apr. 2015, vol. 6, pp. 109-120.
Chilton et al. "Effects of empagliflozin on blood pressure and makers of arterial stiffness and vascular resistance in patients with type 2 diabetes," Diabetes, Obesity and Metabolism, Dec. 2015, vol. 17, No. 12, pp. 1180-1193.
European Search Report issued in European Patent Application No. 17 84 6468, dated Mar. 26, 2020.
Kitada et al. "Hyperglycemia causes cellular senescence via a SGLT2- and p21-dependent pathway in proximal tubules in the early stage of diabetic nephropathy," Journal of Diabetes and Its Complications, Sep. 3, 2014, vol. 28, No. 5, pp. 604-611.
Nakamura et al. "Insulin Stimulates SGLT2-mediated tubular glucose absorption via oxidative stress generation," Diabetology & Metabolic Syndrome, BioMed Central, 2015, vol. 7, No. 48, pp. 1-6.
Shojima et al. Ipragliflozin, a Novel SGLT2 inhibitor, improves blood glucose, as shown by continuous glucose monitoring, and ameliorates metabolic syndrome in Japanese Patients with Type 2 Diabetes Mellitus, Clinical Diabetes/ Therapeutics POSTERS, Poster No. 1150-P, p. A301.

(Continued)

*Primary Examiner* — Raymond J Henley, III
(74) *Attorney, Agent, or Firm* — Birch, Stewart, Kolasch & Birch, LLP (57) ABSTRACT

The present invention provides an agent or pharmaceutical composition for eliminating senescent cells, comprising an SGLT2 inhibitor.

1 Claim, 7 Drawing Sheets

(56) References Cited

OTHER PUBLICATIONS

Thomas et al. "Long-term treatment with empagliflozin, a novel, potent and selective SGLT-2 inhibitor, improves glycaemic control and features of metabolic syndrome in diabetic rats," Diabetes, Obesity and Metabolism, Jan. 2012, vol. 14, No. 1, pp. 94-96.

* cited by examiner

[Fig. 1]

(a) Normal diet   (b) High fat diet   (c) High fat diet + SGLT2i

Arrows: Macrophage (F4/80 positive)

AGENT FOR ELIMINATING SENESCENT CELLS

TECHNICAL FIELD

The present invention relates to novel use of SGLT2 inhibitors.

BACKGROUND ART

The numbers of patients suffering from obesity and diabetes are increasing due to an excessive caloric intake and such fact becomes a serious social issue. Obesity and diabetes are known to cause chronic inflammation mediated by cellular senescence at visceral adipose tissues and induce systemic metabolic failure. In addition, inhibition of senescence of adipocytes has been reported to improve adipose inflammation and inhibit systemic metabolic failure associated with obesity (for example, see NPL 1).

CITATION LIST

Non Patent Literature

[NPL 1] Minamino, T., et al., A crucial role for adipose tissue p53 in the regulation of insulin resistance, Nat. Med., 15, 1082-1087, 2009.

SUMMARY OF INVENTION

Technical Problem

Under the above circumstance, there is a need for a technique to eliminate senescent cells. Therefore, an object of the present invention is to provide an agent for eliminating senescent cells.

Solution to Problem

The present inventor has conducted extensive studies in view of the problem and has found that a sodium glucose co-transporter 2 (hereinafter referred to as "SGLT2") inhibitor, known as an agent for treating diabetes, had an activity to eliminate senescent cells, thereby completing the invention.

In other words, a summary of the present invention is as follows:
[1] An agent for eliminating senescent cells, comprising an SGLT2 inhibitor.
[2] The agent for eliminating senescent cells of the above-mentioned [1], wherein the SGLT 2 inhibitor is at least one selected from the group consisting of low molecular weight compounds, SGLT2 expression inhibitors, and SGLT2-specific binding substances.
[3] The agent for eliminating senescent cells of the above-mentioned [1] or [2], wherein the SGLT 2 inhibitor is at least one selected from the group consisting of canagliflozin, empagliflozin, ipragliflozin, dapagliflozin, luseogliflozin, tofogliflozin, sergliflozin etabonate, remogliflozin etabonate, ertugliflozin, sotagliflozin, and pharmaceutically acceptable salts thereof.
[4] A pharmaceutical composition for eliminating senescent cells, comprising an SGLT2 inhibitor and a pharmaceutically acceptable carrier.
[5] The pharmaceutical composition of the above-mentioned [4], wherein the composition is for preventing or treating a disease in which the disease state is expected to be improved by eliminating the senescent cells.
[6] The pharmaceutical composition of the above-mentioned [5], wherein the disease in which the disease state is expected to be improved by eliminating the senescent cells is a senescence-related disease.
[7] A pharmaceutical composition for use in the prevention or treatment of a senescence-related disease, comprising an SGLT2 inhibitor and a pharmaceutically acceptable carrier.
[8] The pharmaceutical composition of the above-mentioned [6] or [7], wherein the senescence-related disease is at least one selected from the group consisting of heart failure, arteriosclerosis, arteriosclerotic cerebrovascular or cardiovascular disease, hypertension, cerebral infarction, cerebral hemorrhage, dyslipidemia, pulmonary fibrosis, emphysema, skeletal muscle atrophy (sarcopenia), osteoarthritis, dementia, frailty, cancer, chronic kidney disease, cataract, glaucoma, age-related macular degeneration, presbyopia, age-related alopecia, age-related hearing loss, pain associated with aging such as lumbar pain and joint pain, asteatotic eczema, cutaneous pruritus, fatty liver, nonalcoholic steatohepatitis (NASH), liver cirrhosis, osteoporosis, osteoarthropathy, Hutchinson-Gilford progeria syndrome, Werner syndrome, Cockayne syndrome, and Rothmund-Thomson syndrome.
[9] The pharmaceutical composition of any of the above-mentioned [4]-[8], wherein the SGLT 2 inhibitor is at least one selected from the group consisting of canagliflozin, empagliflozin, ipragliflozin, dapagliflozin, luseogliflozin, tofogliflozin, sergliflozin etabonate, remogliflozin etabonate, ertugliflozin, sotagliflozin, and pharmaceutically acceptable salts thereof.
[10] Use of an SGLT2 inhibitor in the manufacture of a medicament for eliminating senescent cells.
[11] Use of an SGLT2 inhibitor in the manufacture of a medicament for preventing or treating a disease in which the disease state is expected to be improved by eliminating senescent cells.
[12] A method for eliminating senescent cells, comprising administrating an effective amount of an SGLT2 inhibitor to a subject in need thereof.
[13] A method for preventing or treating a disease in which the disease state is expected to be improved by eliminating senescent cells, comprising administrating an effective amount of an SGLT2 inhibitor to a subject in need thereof.

Advantageous Effects of Invention

According to the present invention, senescent cells can be eliminated and a disease in which the disease state is expected to be improved by eliminating the senescent cells can be prevented and/or treated.

BRIEF DESCRIPTION OF DRAWINGS

FIG. 1(a) shows the result for the normal diet group mice. The scale bar indicates 5 mm. FIG. 1(b) shows the result for the high fat diet group mice. FIG. 1(c) shows the result for the high fat diet+SGLT2i group mice.

FIG. 3 is graphs showing the results of quantitative RT-PCR (Experimental Example 4). The data are presented as mean±2 SE (n=6). NC: normal diet, HFD: high fat diet, Si3d: SGLT2 inhibitor administration for 3 days, Si7d: SGLT2 inhibitor administration for 7 days. *P<0.05, **P<0.01 (tested by Tukey's multiple comparison test after one-way ANOVA).

FIG. 4(a) is photographs showing the results of HE staining. The scale bar indicates 200 μm. FIG. 4(b) is a graph showing the result of counting CLS number. (Experimental Example 5) The data are presented as mean±2 SE (n=6). NC: normal diet, HFD: high fat diet, Si7d: SGLT2 inhibitor administration for 7 days. **P<0.01 (tested by Tukey's multiple comparison test after one-way ANOVA).

FIG. 5(a) is photographs showing the results of evaluating oxidative stress by DHE staining. The scale bar indicates 100 μm. FIG. 5(b) is a graph of the result of measuring DHE positive area. (Experimental Example 5) The data are presented as mean±2 SE (n=6). NC: normal diet, HFD: high fat diet, Si7d: SGLT2 inhibitor administration for 7 days. *P<0.05, **P<0.01 (tested by Tukey's multiple comparison test after one-way ANOVA).

FIG. 6(a) is graphs of the results of quantitative RT-PCR. The data are presented as mean±2 SE (n=6). NC: normal diet, HFD: high fat diet, Si3d: SGLT2 inhibitor administration for 3 days, Si7d: SGLT2 inhibitor administration for 7 days. *P<0.05 (tested by Tukey's multiple comparison test after one-way ANOVA). FIG. 6(b) is photographs showing immunofluorescence staining with F4/80. The data are presented as mean±2 SE (n=3). NC: normal diet, HFD: high fat diet, Si3d: SGLT2 inhibitor administration for 3 days, Si7d: SGLT2 inhibitor administration for 7 days. *P<0.05 (tested by Tukey's multiple comparison test after one-way ANOVA). (Experimental Example 5)

FIG. 7 is graphs showing the results of quantitative RT-PCR (Experimental Example 6). The data are presented as mean±2 SE (n=5 or 6). NC: normal diet, HFD: high fat diet, Si7d: SGLT2 inhibitor administration for 7 days. *P<0.05, **P<0.01 (tested by Tukey's multiple comparison test after one-way ANOVA).

DESCRIPTION OF EMBODIMENTS

In one embodiment, the present invention provides an agent or pharmaceutical composition for eliminating senescent cells, comprising an SGLT2 inhibitor.

In another embodiment, the present invention provides a medicament for eliminating senescent cells or use of an SGLT2 inhibitor in the manufacture of a medicament for preventing or treating a disease in which the disease state is expected to be improved by eliminating senescent cells.

In yet another embodiment, the present invention provides a method for eliminating senescent cells or for preventing or treating a disease in which the disease state is expected to be improved by eliminating senescent cells, which method comprises administering an effective amount of an SGLT2 inhibitor to a subject in need thereof.

In still yet another embodiment, the present invention provides an SGLT2 inhibitor for use in eliminating senescent cells or for use in preventing or treating a disease in which the disease state is expected to be improved by eliminating senescent cells.

In a particularly preferred embodiment, the above-mentioned agent, pharmaceutical composition, medicament, and the like contain the SGLT2 inhibitor as an active ingredient.

Senescent Cell

The "senescent cell" herein refers to a cell that presents increased expression amount of a senescence marker as compared to a normal cell. The senescence marker includes senescence-associated acidic β-galactosidase, p53, $p15^{INK4a}$, $p21^{CIP1}$, and the like. The senescent cell is characterized by irreversible cessation of growth at G1 phase and is known to be formed due to suppression of genes that stimulate progression of the cell cycle and increased expression of p53, $p16^{INK4a}$, and $p21^{CIP1}$ that inhibit the cell cycle.

The senescent cell may be a cell which has been arrested in the process of division but remains metabolically active. Non-dividing cells can survive for weeks but cannot proliferate and replicate DNA despite the presence of sufficient space, nutrients, and growth factors in the medium. Thus, this cessation of the division is essentially permanent since the senescent cells cannot be stimulated and proliferated even if physiological stimuli are applied to them.

The senescent cells can differ from the non-senescent cells in one or more of the following points: 1) the senescent cells stop proliferating and cannot be stimulated so as to reenter the cell cycle with physiological mitogens; 2) the senescent cells become resistant to apoptotic cell death; and 3) the senescent cells acquire altered differentiation functions.

The senescent cell may result from replicative cell senescence, premature cell senescence, therapeutically-induced cell senescence, and the like. The senescent cell resulting from replicative cell senescence may have undergone multiple cell divisions, e.g., 40 or more, 50 or more, 60 or more, 70 or more, or 80 or more cell divisions. The senescent cell resulting from premature cell senescence may be induced by, but not limited to, ultraviolet radiation, reactive oxygen species, environmental toxins, smoking, ionizing radiation, distortion of chromatin structure, excess mitogenic signaling, carcinogenic mutations, and the like. In certain embodiments, premature cell senescence can be induced by ionizing radiation. In another certain embodiment, premature cell senescence can be induced by ectopic transfected Ras protein. The senescent cell resulting from treatment-induced cell senescence may be induced by radiation therapy, chemotherapy, DNA damaging therapy, and the like.

The senescent cells to be subjected by the present invention may generally be eukaryotic cells. Examples of the senescent cells include, but are not limited to, mammary epithelial cells, keratinocytes, cardiomyocytes, chondrocytes, endothelial cells (macrovessels), endothelial cells (microvessels), epithelial cells, fibroblasts, dermal papilla cells, hepatocytes, melanocytes, osteoblasts, preadipocytes, cells in immune system, skeletal muscle cells, smooth muscle cells, adipocytes, neurons, glial cells, contractile cells, exocrine epithelial cells, extracellular matrix cells, cells secreting hormones, keratotic cells, islet cells, lens cells, mesenchymal stem cells, pancreatic adenocarcinoma cells, small intestinal Paneth cells, cells in hematopoietic system, cells in nervous system, cells supporting sensory organs or peripheral nerve cells, and wet stratified barrier epithelial cells.

In addition, the senescent cells to be subjected by the present invention may also be found in regenerative tissues, including vascular system, hematopoietic system, epithelial organs, and stroma. The senescent cells may also be found at senile sites or sites in chronic conditions associated with senescence such as osteoarthritis and atherosclerosis. In addition, the senescent cells may be associated with benign dysplastic lesions, precancerous lesions, or benign prostatic hyperplasia. In one embodiment, the senescent cells may be found in normal and/or tumor tissues after DNA damaging therapy. In another certain embodiment, the senescent cells may be found at sites in disease states associated with senescence.

The number of senescent cells in various organs and tissues usually increases with age. Accumulation of the senescent cells may advance senescence and degradation under senescence-related diseases. For example, accumulation of the senescent cells in senescent tissue may contribute to age-related tissue dysfunction, decreased regenerative capacity, and diseases. In one embodiment, the senescent tissue in which the senescent cells have accumulated lacks the ability to respond to stress in which proliferation is required, which results in the decrease in health which could be seen with aging.

Eliminating Senescent Cells

The "eliminating senescent cells" herein means removing the senescent cells from tissues, organs, or the like, or killing the senescent cells. It is particularly preferable that cells which are not the senescent cells (hereinafter referred to as "non-senescent cells") are not significantly killed but the senescent cells are selectively or specifically killed, at the same concentration.

Therefore, the 50% lethal concentration (Lethal Concentration 50, hereinafter referred to as "LC50") of the SGLT2 inhibitor used in the present invention in the non-senescent cells may preferably be about 2 to about 50 times higher than the LC50 of said SGLT2 inhibitor in the senescent cells. LC50 is the concentration required to kill half of the cells in cell samples. For example, the LC50 in the non-senescent cells may be about 2 times or more, about 3 times or more, about 4 times or more, about 5 times or more, about 6 times or more, about 7 times or more, about 8 times or more, about 9 times or more, about 10 times or more, or higher than the LC50 in the senescent cells. Alternatively, the LC50 in the non-senescent cells may be about 10 times or more, about 15 times or more, about 20 times or more, about 25 times or more, about 30 times or more, about 35 times or more, about 40 times or more, about 45 times or more, about 50 times or more, or higher than the LC50 in the senescent cells.

Accumulation of senescent cells is known to promote disease states of senescence-related diseases and the like. Thus, diseases in which the disease state is expected to be improved by eliminating senescent cells, such as senescence-related diseases, can be prevented or treated by administering the agent or pharmaceutical composition for eliminating senescent cells according to the present invention, thereby eliminating the senescent cells.

Senescence-Related Diseases

The "senescence-related diseases" herein can include any disease or condition that is totally or partially mediated by the induction or maintenance of a non-proliferative or senescent condition in a cell or cell population in a subject. The senescence-related diseases may include tissue or organ degeneration in which signs of the disease condition are not visible, and visible disease conditions such as degenerative diseases or hypofunctions.

Examples of the senescence-related diseases include Alzheimer's disease, Parkinson's disease, cataract, macular degeneration, glaucoma, atherosclerosis, acute coronary syndrome, myocardial infarction, stroke, hypertension, idiopathic pulmonary fibrosis (IPF), chronic obstructive pulmonary disease (COPD), osteoarthritis, coronary artery disease, cerebrovascular disease, periodontal disease, atrophy or fibrosis in various tissues, brain or heart injury, treatment-related myelodysplastic syndrome, and the like. The senescence-related diseases may also include Hutchinson-Gilford progeria syndrome, Werner syndrome, Cockayne syndrome, xeroderma pigmentosum, ataxia telangiectasia, Fanconi anemia, neuropathic anemia, and the like.

Further examples of the senescence-related diseases include circulatory diseases, such as cardiovascular diseases, e.g. angina pectoris, aortic aneurysms, arrhythmia, cerebral aneurysms, diastolic dysfunction, cardiac fibrosis, cardiomyopathy, carotid artery disease, coronary thrombosis, endocarditis, hypercholesterolemia, hyperlipidemia, mitral valve prolapse, and peripheral vascular disease; inflammatory or autoimmune diseases, such as disc herniation, oral mucositis, erythema, interstitial cystitis, scleroderma, and alopecia; neurodegenerative diseases, such as dementia, Huntington's disease, motor neuron dysfunction, memory loss associated with aging, depression, and mood disorder, metabolic disease such as metabolic syndrome; pulmonary diseases, such as decreased pulmonary function associated with aging, asthma, bronchiectasis, cystic fibrosis, and emphysema; gastrointestinal diseases such as Barrett's esophagus; diseases associated with aging, such as hepatic fibrosis, muscle fatigue, oral mucosa fibrosis, pancreatic fibrosis, benign prostatic hyperplasia (BPH), and sleep disorder, reproductive failure, such as climacterium, decreased ovum supply, decreased sperm viability, decreased fertility, decreased libido, decreased erection, and excitation; skin diseases, such as atopic dermatitis, skin erythema, cutaneous lymphoma, dysesthesia, eczema, eosinophilic dermatitis, fibrotic proliferation of skin, hyperpigmentation, immuno blistering disease, nevus, pemphigus vulgaris, itching, psoriasis, rash, reactive neutrophilic skin disease, wrinkles, and urticaria; posttransplant kidney fibrosis; carotid artery thrombosis; and the like.

Furthermore, preferred examples of the senescence-related diseases include circulatory diseases, such as heart failure, atherosclerosis, arteriosclerotic cerebrovascular or cardiovascular disease, and hypertension; cerebrovascular diseases, such as cerebral infarction and cerebral hemorrhage; metabolic diseases such as dyslipidemia; respiratory diseases, such as pulmonary fibrosis and emphysema; locomotive syndromes, such as skeletal muscle atrophy (sarcopenia) and osteoarthritis; geriatric syndromes, such as dementia and frailty, cancer, chronic kidney disease; ocular diseases, such as cataract, glaucoma, age-related macular degeneration, and presbyopia; age-related alopecia; age-related hearing loss; pain associated with aging, such as lumbar pain and joint pain; skin diseases, such as asteatotic eczema and cutaneous pruritus; liver diseases, such as fatty liver, nonalcoholic steatohepatitis (NASH), and liver cirrhosis; bone diseases, such as osteoporosis and osteoarthropathy; premature aging, such as Hutchinson-Gilford progeria syndrome, Werner syndrome, Cockayne syndrome, and Rothmund-Thomson syndrome; and the like.

SGLT2 Inhibitors

The SGLT2 inhibitors used in the present invention include drugs that inhibit reabsorption of glucose by SGLT2. More specific SGLT2 inhibitors include low molecular weight compounds, SGLT2 expression inhibitors, SGLT2-specific binding substances, and the like.

Low Molecular Weight Compounds

The low molecular weight compounds that are the SGLT2 inhibitors include, for example, canagliflozin [(1S)-1,5-Anhydro-1-C(-3 {[5-(4-fluorophenyl)thiophen-2-yl]methyl}-4-methylphenyl)-D-glucitol], empagliflozin [(1S)-1,5-Anhydro-1-C-{4-chloro-3-[(4-{[(3S)-oxolan-3-yl]oxy}phenyl)methyl]phenyl}-D-glucitol], ipragliflozin [(1 S)-1,5-Anhydro-1-C-{3-[(1-benzothiophen-2-yl)methyl]-4-fluorophenyl}-D-glucitol], dapagliflozin [(1S)-1,5-Anhydro-1-C-{4-chloro-3-[(4-ethoxyphenyl)methyl]phenyl}-D-glucitol], luseogliflozin [(2S,3R,4R,5S,6R)-2-{5-[(4-Ethoxyphenyl)methyl]-2-methoxy-4-methylphenyl}-6-(hydroxymethyl)thiane-3,4,5-triol], tofogliflozin [(1 S,3'R,4'S,5'S,6'R)-6-[(4-Ethylphenyl)methyl]-6'-(hydroxymethyl)-3',4',5',6'-tetrahydro-3H-spiro[2-benzofuran-1,2'-pyran]-3',4',5'-triol], sergliflozin etabonate [2-(4-Methoxybenzyl)phenyl 6-O-(ethoxycarbonyl)-β-D-glucopyranoside], remogliflozin etabonate [5-Methyl-1-(propan-2-yl)-4-[[4-[(propan-2-yl)oxy]phenyl]methyl]-1H-pyrazol-3-yl 6-O-(ethoxycarbonyl)-β-D-glucopyranoside], ertugliflozin [(1 S,2S,3S,4R,5S)-5-[4-Chloro-3-[(4-ethoxyphenyl)methyl]phenyl]-1-(hydroxymethyl)-6,8-dioxabicyclo[3.2.1]octane-2,3,4-triol], sotagliflozin [Methyl (5S)-5-C-[4-chloro-3-[(4-ethoxyphenyl)methyl]phenyl]-1-thio-β-L-xylopyranoside], and pharmaceutically acceptable salts thereof. These compounds can be produced by known production methods or by any production methods in which the known production methods are modified.

The pharmaceutically acceptable salts of the low molecular weight compounds that are the SGLT2 inhibitors include, for example, salts with alkali metals such as lithium, sodium, and potassium; salts with Group 2 metals such as calcium and magnesium; salts with zinc or aluminum; salts with amines such as ammonia, choline, diethanolamine, lysine, ethylenediamine, t-butylamine, t-octylamine, tris(hydroxymethyl)aminomethane, N-methyl-glucosamine, triethanolamine, and dehydroabiethylamine; salts with inorganic acids such as hydrochloric acid, hydrobromic acid, hydroiodic acid, sulfuric acid, nitric acid, and phosphoric acid; salts with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, and benzenesulfonic acid; salts with acidic amino acids such as aspartic acid and glutamic acid; and the like.

In addition, the pharmaceutically acceptable salts of the low molecular weight compounds that are the SGLT2 inhibitors include intramolecular salts, hydrates, and cocrystals with L-proline, etc., solvates with (2S)-propane-1,2-diol, etc., and the like, of the low molecular weight compounds.

SGLT2 Expression Inhibitors

The SGLT2 expression inhibitors include, for example, siRNA, shRNA, miRNA, ribozymes, antisense nucleic acids, low molecular weight compounds, and the like. Expression of SGLT2 can be inhibited by administering such expression inhibitors.

siRNA (small interfering RNA) is a small double-stranded RNA consisting of 21 to 23 base pairs that is used for gene silencing by RNA interference.

siRNA binds to RNA-induced silencing complex (RISC) after having been introduced into a cell. This complex binds to and cleaves mRNA having a sequence complementary to the siRNA. As a result, gene expression is suppressed in a sequence-specific manner.

siRNA can be produced by synthesizing a sense strand oligonucleotide and an antisense strand oligonucleotide respectively using a DNA/RNA automated synthesizer, and then, for example, denaturing them for about 1 minute at 90° C. to 95° C. in a suitable annealing buffer and annealing them for about 1 to 8 hours at 30° C. to 70° C.

Short hairpin RNA (shRNA) is a hairpin RNA sequence that is used for gene silencing by RNA interference. shRNA may be introduced into a cell with a vector and expressed with a U6 promoter or H1 promoter, or may be prepared by synthesizing an oligonucleotide having an shRNA sequence using a DNA/RNA automated synthesizer and self-annealing the obtained oligonucleotides using the similar method as that of siRNA. The hairpin structure of shRNA introduced into the cell is cleaved to siRNA and binds to RNA-induced silencing complex (RISC). This complex binds to and cleaves mRNA having a sequence complementary to the siRNA. As a result, gene expression is suppressed in a sequence-specific manner.

miRNA (microRNA) is a functional nucleic acid that is encoded on a genome and finally becomes microRNA consisting of about 20 bases through a multistage formation process. miRNA is classified as a functional ncRNA (non-coding RNA, a generic term for RNA that will not be translated into protein) and plays an important role in the biological phenomenon in respect of the regulation of expression of other genes. Administration of miRNA having a specific base sequence into a living body can inhibit SGLT2 expression.

Ribozyme is an RNA that has catalytic activity. Ribozymes have various types of activity, and study on ribozymes as enzymes that cleave RNA allows us to design ribozymes for the purpose of site-specific cleavage of RNA. Ribozyme may consist of 400 nucleotides or more, such as Group I intron and M RNA contained in RNaseP, or may consist of about 40 nucleotides such as the hammerhead or the hairpin.

The antisense nucleic acid is a nucleic acid complementary to a target sequence. The antisense nucleic acid can inhibit expression of a target gene by: inhibiting initiation of transcription by forming a triplex; suppressing transcription by forming a hybrid with a site where an open loop structure has been locally formed by RNA polymerase; inhibiting transcription by forming a hybrid with RNA which is about to be synthesized; suppressing splicing by forming a hybrid at the intron-exon junction; suppressing splicing by forming a hybrid with a spliceosome formation site; suppressing migration from the nucleus to the cytoplasm by forming a hybrid with mRNA; suppressing splicing by forming a hybrid with a capping site or poly(A) addition site; suppressing initiation of translation by forming a hybrid with a translation initiation factor binding site; suppressing translation by forming a hybrid with a ribosome binding site near the start codon; inhibiting peptide chain elongation by forming a hybrid with an mRNA coding region or polysome binding site; suppressing gene expression by forming a hybrid with an interaction site between a nucleic acid and protein; or the like.

The siRNA, shRNA, miRNA, ribozyme, and antisense nucleic acid may contain various chemical modifications so as to improve stability or activity. For example, a phosphate residue may be substituted with a chemically-modified phosphate residue, such as phosphorothioate (PS), methylphosphonate and phosphorodithionate, in order to prevent decomposition by hydrolases such as nucleases. In addition, at least a portion thereof may be composed of a nucleic acid analog such as peptide nucleic acid (PNA).

SGLT2-Specific Binding Substances

The SGLT2-specific binding substances include substances that specifically bind to SGLT2 and inhibit the function thereof, for example, antibodies, antibody fragments, aptamers, and the like. For example, the antibody can be prepared by immunizing an animal such as a mouse with SGLT2 protein or a fragment thereof as an antigen. Alternatively, for example, the antibody can be prepared by screening a phage library. The antibody fragment includes Fv, Fab, scFv, and the like. The antibody is preferably a monoclonal antibody. In addition, the antibody may be a commercially available antibody. The aptamer is a substance having an ability to bind specifically to a target substance. The aptamer includes a nucleic acid aptamer, a peptide aptamer, and the like. The nucleic acid aptamer having an ability to bind specifically to a target peptide can be selected by, for example, a technique such as systematic evolution of ligand by exponential enrichment (SELEX), and the like. In addition, the peptide aptamer having an ability to bind specifically to a target peptide can be selected by, for example, a technique such as the two-hybrid method using yeast, and the like.

In one embodiment, the present invention provides a pharmaceutical composition for eliminating senescent cells, comprising the SGLT2 inhibitor and a pharmaceutically acceptable carrier. The senescent cells can be eliminated by administering the pharmaceutical composition of this embodiment. In addition, by eliminating the senescent cells, diseases in which the disease state is expected to be improved by eliminating senescent cells, preferably senescence-related diseases, can also be prevented or treated. Namely, this embodiment also provides pharmaceutical compositions for the prevention or treatment of diseases in which the disease state is expected to be improved by eliminating senescent cells.

The pharmaceutical composition of this embodiment may be formulated into a dosage form to be used orally or parenterally. For example, the dosage form to be used orally includes a tablet, a capsule, an elixir, a microcapsule, and the like. For example, the dosage form to be used parenterally includes an injection, an ointment, a patch, and the like.

As the pharmaceutically acceptable carrier, any carriers can be used without any particular limitations as long as they are conventionally used in the preparation of pharmaceutical compositions. For example, more specific examples thereof include binders, such as gelatin, cornstarch, tragacanth gum, and gum arabic; excipients such as starch and crystalline cellulose; swelling agents such as alginate; injection solvents, such as water, ethanol, and glycerin; adhesives such as rubber-based adhesives and silicone-based adhesives; and the like.

The pharmaceutical composition may contain an additive. The additive includes a lubricant such as calcium stearate and magnesium stearate; a sweetener, such as sucrose, lactose, saccharin, and maltitol; a flavoring agent such as peppermint and wintergreen oil; a stabilizer such as benzyl alcohol and phenol; a buffer such as phosphate and sodium acetate; a solubilizing agent such as benzyl benzoate and benzyl alcohol; an antioxidant; a preservative; and the like.

The pharmaceutical composition can be formulated by suitably combining the SGLT2 inhibitor, the pharmaceutically acceptable carrier, and where necessary, the additive, and mixing them in a unit dosage form required for a generally accepted pharmaceutical implementation.

The subjects to which the SGLT2 inhibitors are administered include, but are not limited to, humans, monkeys, dogs, cows, horses, sheep, pigs, rabbits, mice, rats, guinea pigs, hamsters, and cells thereof. Among these, mammals or mammalian cells are preferable, and human or human cells are particularly preferable.

The dose of the SGLT2 inhibitor cannot be determined uniformly since it varies according to the specific subject to be administered, and the symptom, body weight, age, gender, or the like, of the subject. In the case of oral administration, for example, about 0.1 mg to about 100 mg/kg body weight of the SGLT2 inhibitor may be administered per a unit dosage form for adults. In the case of the injection, for example, about 0.01 mg to about 50 mg of the SGLT2 inhibitor may be administered per a unit dosage form for adults.

In addition, the daily dose of the SGLT2 inhibitor cannot be determined uniformly since it varies according to the specific subject to be administered, and the symptom, body weight, age, gender, or the like, of the subject. For example, about 0.1 mg to about 100 mg/kg body weight/day of the SGLT2 inhibitor may be administered once a day or divided into about two to three times per day for adults.

The SGLT2 inhibitor according to the present invention may be used in combination with at least one agent selected from the group consisting of agents for eliminating senescent cells other than the SGLT2 inhibitors and other therapeutic agents for diseases. The SGLT2 inhibitor and the other agent can be in the same formulation or be in separate formulations. In addition, each formulation can be administered by the same administration route or by separate administration routes. The administration routes include, for example, oral and injection. Further, each formulation can be administered simultaneously, sequentially, or separately with a time or period interval. In one embodiment, the SGLT2 inhibitor and the other agent may be into a kit comprising them.

EXAMPLES

The present invention is described hereinafter in more detail by use of Examples, and however, the following Examples should not limit the present invention in any way.

Experimental Example 1

Preparation of Obesity Model Mice

Four-week-old wild-type mice (C57BL/6NCr) were fed with high fat diets for 8 weeks to prepare diet-induced obesity model mice. Then, canagliflozin, an SGLT2 inhibitor, was administered orally to the prepared obesity model mice by mixing with the diet at the concentration of 0.03% w/w (hereinafter referred to as "high fat diet+SGLT2i group").

For comparison, four-week-old wild-type mice (C57BL/6NCr) fed with normal diets for 8 weeks (hereinafter referred as "normal diet group") and obesity model mice prepared in the same manner as described above with the exception of not administering canagliflozin (hereinafter referred to as "high fat diet group") were prepared.

Experimental Example 2

Study on Senescence-Associated Acidic β-Galactosidase Activity

The visceral adipose tissues (epididymal adipose tissues) were collected from the mice of each group one week after starting administration of canagliflozin in Experimental Example 1.

Then, the senescent cells in the visceral adipose tissues collected from the mice of each group were detected according to the conventional method (Dimri, G. P. et al., Proc. Natl. Acad. Sci. U.S.A., 92(20), 9363-9367, 1995). Specifically, each of the visceral adipose tissues was stained with senescence-associated acidic β-galactosidase and the senescent cells were detected. The senescent cells were stained blue by this staining.

Figure 1:
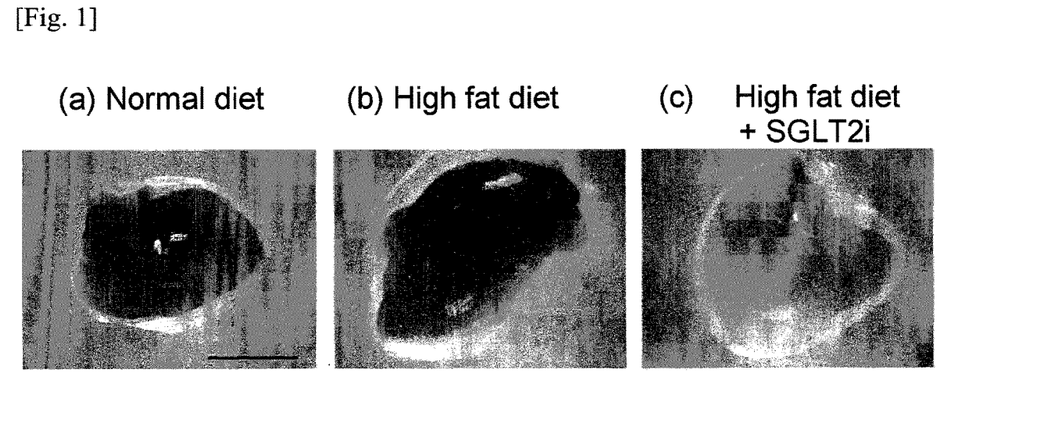
FIGS. 1(a) to (c) are photographs showing the results of senescence-associated acidic β-galactosidase staining (Experimental Example 2).

The results are shown in FIGS. 1(a) to 1(c). FIG. 1(a) shows the result for the mice of the normal diet group. The scale bar indicates 5 mm. FIG. 1(b) shows the result for the mice of the high fat diet group. FIG. 1(c) shows the result for the mice of the high fat diet+SGLT2i group.

As a result, it was shown that administration of the SGLT2 inhibitor significantly decreased the senescent cells in the visceral adipose tissue within the short period of one week. The senescent cells were decreased within the short period, and therefore, administration of the SGLT2 inhibitor was considered to have eliminated the senescent cells. In addition, alleviation of inflammation at the visceral fat was also observed in the mice of the high fat diet+SGLT2i group.

Experimental Example 3

Study on Expression Level of p53 Protein p53 protein is known to play a central role as a senescence accelerating molecule that accelerates cellular senescence. The inventor has previously shown that the cellular senescence reaction through an increase of p53 signal in the visceral adipose tissue was accelerated by adding obesity stress, thereby inducing inflammation of the visceral fat, causing systemic dysmetabolism, and forming or deteriorating the disease state of diabetes. Therefore, expression of p53 protein in adipose tissues of obesity model mice was examined.

Specifically, expression level of p53 protein was measured by Western blotting using a portion of the visceral adipose tissues collected in Experimental Example 2. Type 1C12 (CST) was used as the anti-p53 antibody. Anti-β-actin antibody (type 13E5, CST) was used as the antibody to detect β-actin protein, which is the loading control.

Figure 2:
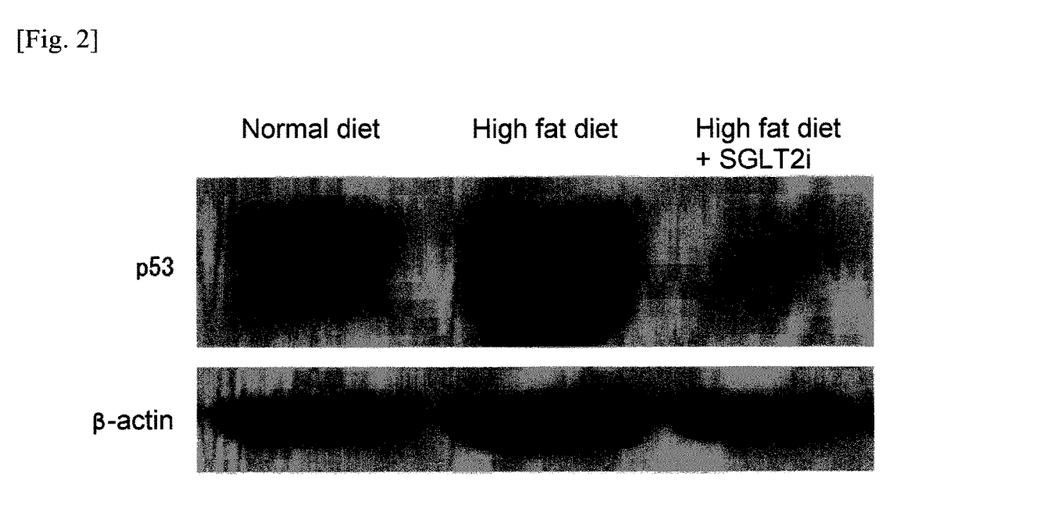
FIG. 2 is photographs showing the results of Western blotting (Experimental Example 3).

FIG. 2 is photographs showing the results of the Western blotting.

As a result, it has been shown that the expression level of p53 in the visceral adipose tissue was significantly lowered by administering the SGLT2 inhibitor to the obesity model mice. This result further supports that the senescent cells are eliminated by administering the SGLT2 inhibitor.

Experimental Example 4

Study on mRNA Expression Levels of Senescence Markers p21 (Cdkn1a) and p16 (Cdkn2a)

mRNA expression of p21 and p16, which play important roles as senescence signals, in addition to p53, was examined.

Specifically, RNA was extracted with RNA-Bee™ (Tel-Test) from a portion of the visceral adipose tissue (epididymal adipose tissue) collected from the mice of each group 3 days and 1 week after starting administration of canagliflozin. The collected RNA was quantified by Nanodrop (Thermo), and cDNA was then prepared from 1 μg of the RNA using QuantiTect Reverse Transcription Kit (Quiagen). This cDNA was used to quantify the relative expression of mRNAs of p21 and p16 using Actb as the housekeeping gene by quantitative RT-PCR method using Light Cycler 480 (Roche), and TaqMan Universal Probe Library and the Light Cycler Master (Roche). The primers for each RNA were designed using the Probe finder on the Roche website.

Figure 3:
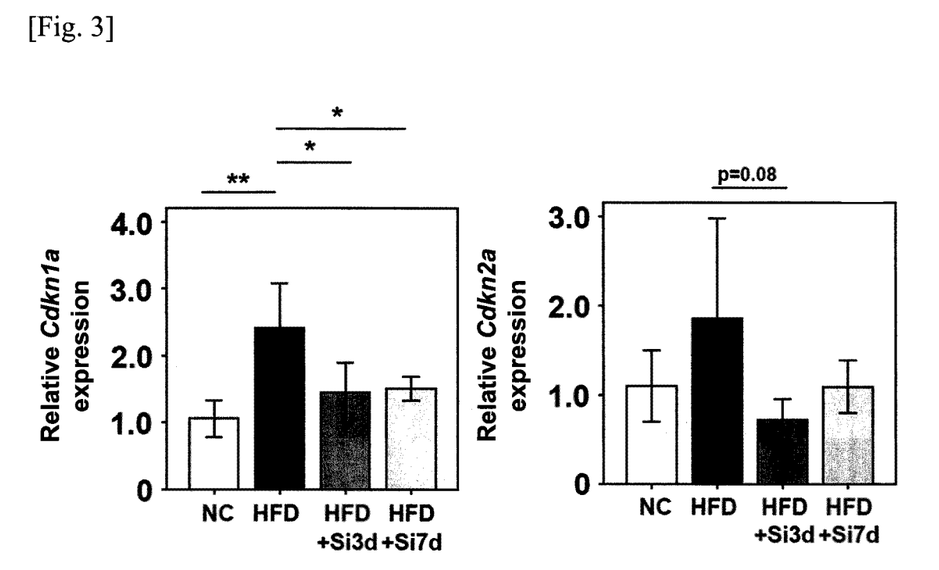

FIG. 3 is graphs showing the results of the quantitative RT-PCR. The administration of the SGLT2 inhibitor significantly suppressed the increase of p21 mRNA levels due to high fat diet-fed, and a similar trend was observed for p16. The results also strongly suggested that the senescent cells were eliminated by the SGLT2 inhibitor.

Experimental Example 5

Study on Effects on Adipose Inflammation and Oxidative Stress in Adipose Tissue

In obese visceral adipose tissues, macrophage-based inflammatory cell infiltration occurs, and a characteristic structure, called crown-like structure (CLS), in which macrophages surround and phagocytose/process adipocytes that have been led to cellular death is observed, and oxidative stress is increased. Therefore, effects of the SGLT2 inhibitor on adipose senescence and adipose inflammation in white adipose tissues of obese model mice were examined.

Specifically, a portion of the visceral fat collected in Experimental Example 4 was immersed and fixed with 10% Mildform (Wako) for at least 24 hours. The sample was dehydrated and embedded in paraffin, and sliced into 5-μm thick. The slices were stuck on slides and subjected to hematoxylin-eosin (HE) staining, dihydroethidium (DHE) staining, or immunofluorescent staining with F4/80 antibody. The stained slices were imaged using Biorevo (Keyence Co.), or where necessary, using confocal microscopy. For the HE staining, the images were photographed at 400× magnification, and the mean number of the crown like structures per one 40× field of view was counted as well. For the DHE staining, the percentage (%) of a red color value equal to or greater than a certain value relative to a randomly photographed 400× image per one field of view was measured using ImageJ. For the Immunofluorescent staining with F4/80 antibody, percentage (%) of F4/80 positive cells per nucleus in one field of view was measured. In addition, mRNAs of CCL2 and TNFα were quantified by quantitative RT-PCR method according to the method described in Experimental Example 4.

Figure 4:
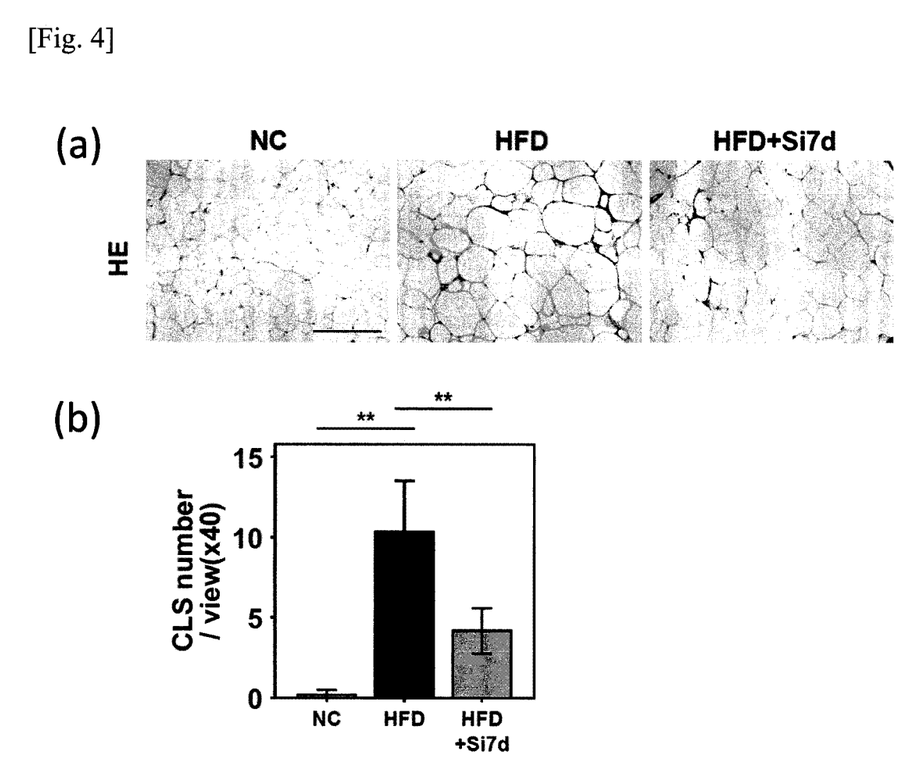

FIG. 4(a) is photographs showing the result of the HE staining. The scale bar indicates 200 μm. FIG. 4(b) is a graph showing the result of counting the number of CLS. The infiltration of macrophages and the CLS structures which had been enhanced by the high fat diet-fed were significantly decreased by administering the SGLT2 inhibitor.

Figure 5:
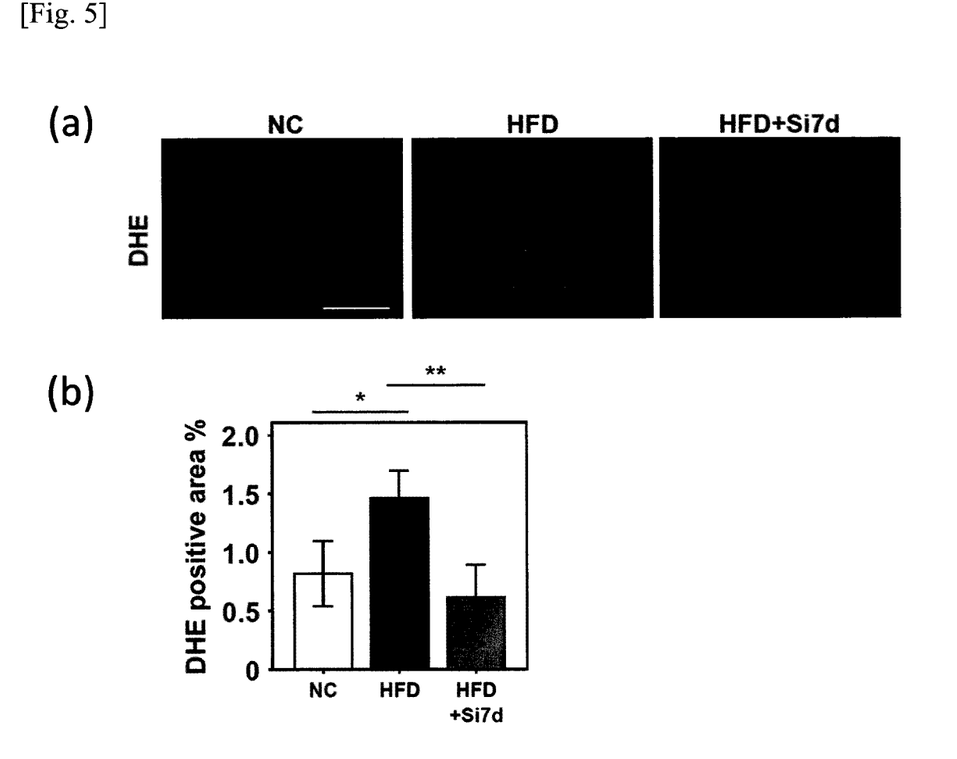

FIG. 5(a) is photographs showing the results of evaluating oxidative stress by the DHE staining. The scale bar indicates 100 μm. FIG. 5(b) is a graph showing the result of measuring the DHE positive area. The oxidative stress which had been enhanced by the high fat diet was also significantly suppressed by administering the SGLT2 inhibitor.

Figure 6:
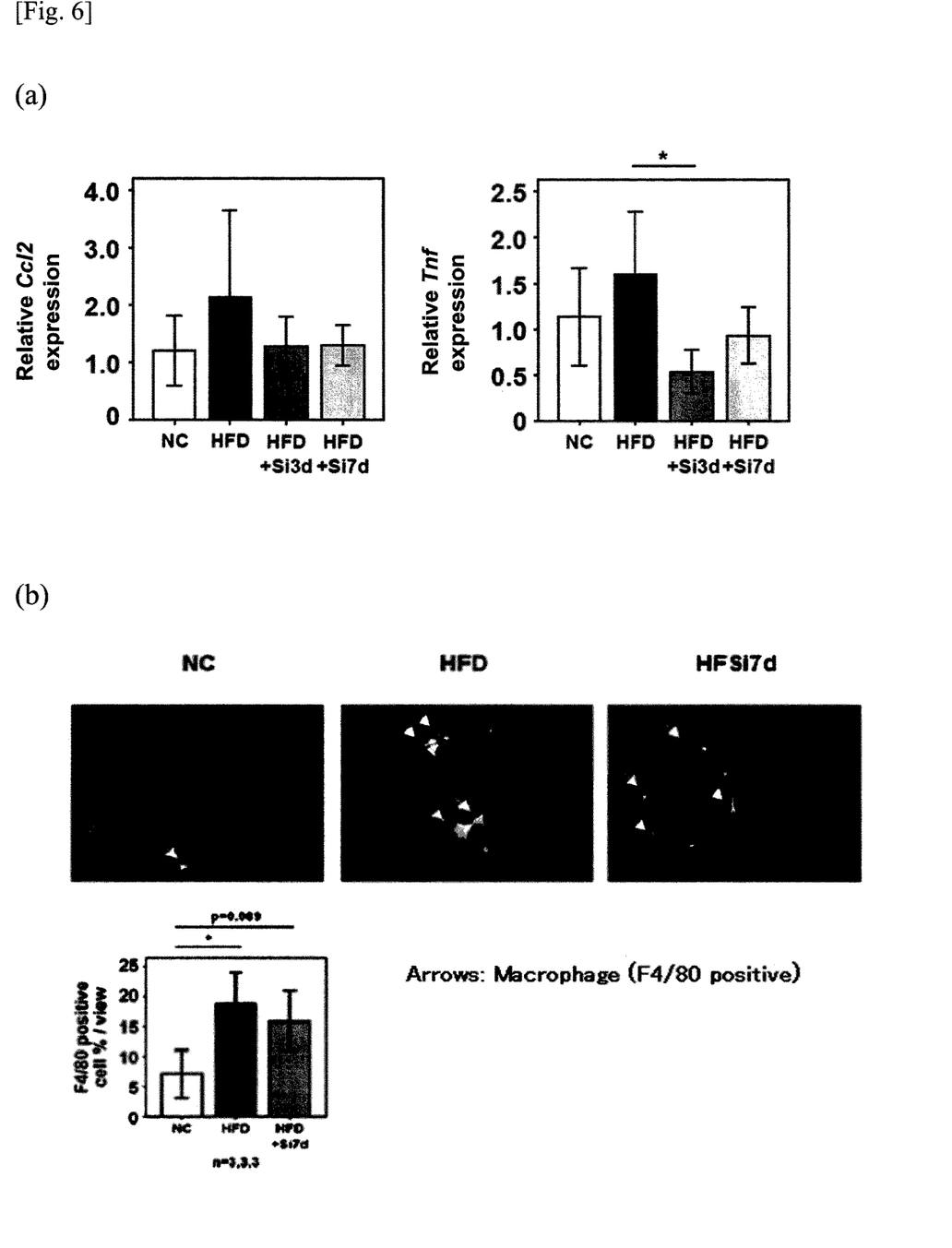

FIG. 6(a) is graphs showing the results of the quantitative RT-PCR. FIG. 6(b) is photographs showing the immunofluorescent staining with F4/80. The administration of the SGLT2 inhibitor tended to decrease the mRNA expression of inflammation-related molecules such as CCL2 and TNFα although macrophage infiltration into adipose tissue remained. From the above results, it was revealed that the SGLT2 inhibitor also decreased adipose inflammation and oxidative stress in obese models as the adipose senescence was improved.

Experimental Example 6

Study on Effects on Senescence Signals in Organs Other than Visceral Adipose Tissue Whether the SGLT2 inhibitor also exerts inhibitory effects on senescence signals in organs other than visceral adipose tissue was examined.

Specifically, mRNA expression levels of p16 and p21 in heart, kidney, skeletal muscle (quadriceps), and brown adipose tissue, which were collected from the same mice when the visceral adipose tissue was collected in Experimental Example 2, were quantified using the same methods described in Experimental Example 4.

Figure 7:
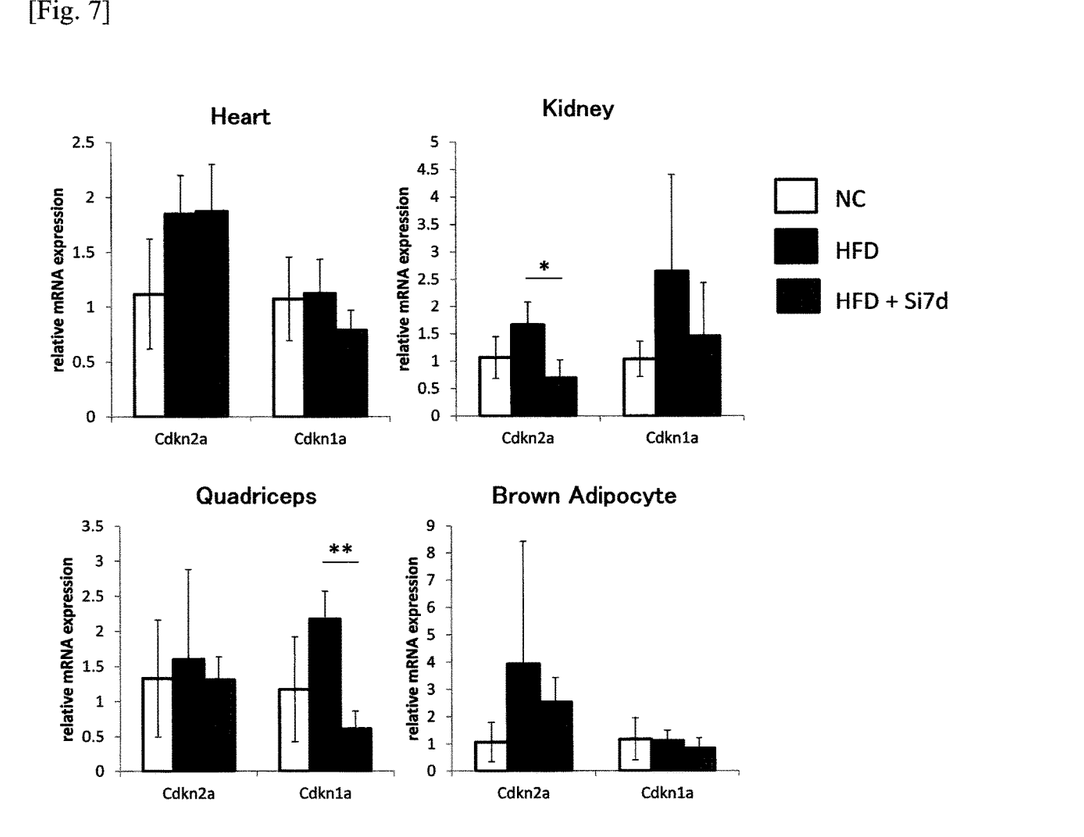

FIG. 7 is graphs showing the results of the quantitative RT-PCR. The administration of the SGLT2 inhibitor tended to decrease mRNA levels of p21 in the heart, p16 and p21 in the kidney, p21 in the skeletal muscle, and p16 in the brown adipose tissue, respectively. From the results, it was considered that the SGLT2 inhibitor exerted the effect of eliminating the senescent cells even in a plurality of organs other than the visceral adipose tissue.

Experimental Example 7

Study in Atherosclerotic Model Mice

Whether the SGLT2 inhibitor exerts an effect to eliminate senescent cells in blood vessels of atherosclerotic model mice was examined.

Four-week-old ApoE-deficient (ApoE$^{-/-}$) mice were fed with high fat diets for 12 weeks, followed by oral administration of canagliflozin, an SGLT2 inhibitor, mixed in the diet at the concentration of 0.03% w/w (hereinafter referred to as "HFD+SGLT2i group"). For comparison, the same mice as described above with the exception of not administering canagliflozin (hereinafter referred to as "HFD group") were prepared. The blood vessels (from the aorta base to the descending aorta on the diaphragm) were collected from the mice of each group 2 weeks after starting administration of canagliflozin. Subsequently, the senescent cells in blood vessels collected from the mice of each group were detected according to the method described in Experimental Example 2. The stainability was measured at a part ranging from the ascending aorta to the branch of the arch left subclavian artery.

Figure 8:
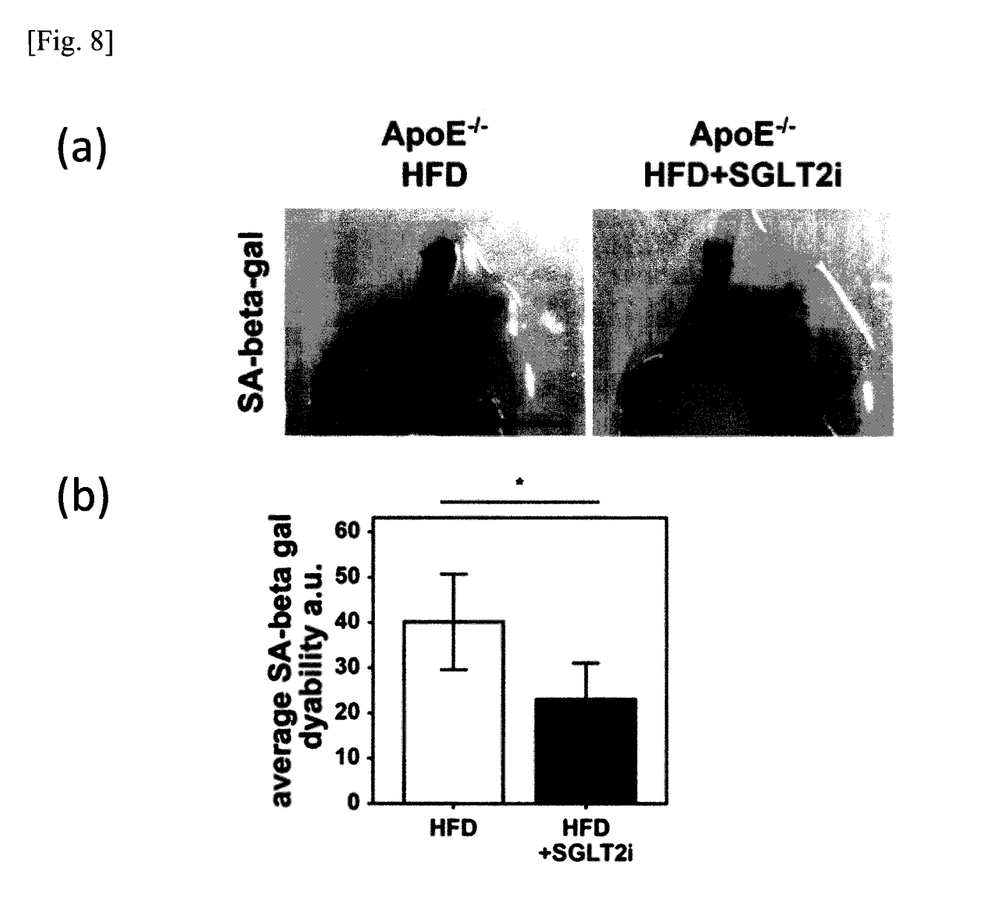
FIG. 8(a) is photographs showing the results of senescence-associated acidic β-galactosidase staining. The scale bar indicates 2 mm.
FIG. 8(b) is a graph showing the results of quantifying the senescence-associated acidic β-galactosidase dyability for blood vessels. The data are presented as mean±2 SE (n=4). * P<0.05 (Student's t-test). (Experimental Example 7)

FIG. 8(a) is photographs showing the results of senescence-associated β-galactosidase staining. The scale bar indicates 2 mm. FIG. 8(b) is a graph showing the results of quantifying the senescence-related β-galactosidase stainability of the blood vessels. The administration of the SGLT2 inhibitor decreased the senescent cells stained blue, and it was shown that the senescent cells were also eliminated in blood vessels.

Experimental Example 8

Study in Progeria Model Mice

Canagliflozin, an SGLT2 inhibitor, mixed in a diet at the concentration of 0.03% w/w was orally administered to 13-week-old Hutchinson-Gilford progeria model mice (Zmpste24-deficient mice), and the general condition of the mice was observed.

When comparing the canagliflozin-treated progeria model mice (hereinafter referred to as "KO+SGLT2i") at 3 to 4 weeks after starting administration of canagliflozin and the progeria model mice without canagliflozin administration (hereinafter referred to as "KO"), deterioration of hair consistency and alopecia were observed in the KO, but they were reduced in the KO+SGLT2i. The results were considered to suggest the possibility of administration of SGLT2 inhibitor to suppress the progress of the disease states of the progeria model mice.

Experimental Example 9

Study in Cultured Senescent Cells

As a result of metabolome analysis of blood and various tissues of mice in which the senescent cells were decreased by short-term administration of the SGLT2 inhibitor, the increase of ketone body concentration in blood and each tissue and the significant increase of AICAR (5-Aminoimidazole-4-carboxamide-1-β-D-ribofuranoside) in blood were observed. It is known that SGLT2 inhibition accelerates fatty acid oxidation and suppresses glycolysis, and that acceleration of glycolysis is observed in senescent cells. Then, whether 3-hydroxybutyrate (hereinafter referred to as "3HB"), AICAR (hereinafter referred to as "AIC"), and 2-deoxyglucose (hereinafter referred to as "2DG") that has an inhibitory effect on glycolysis have effects to induce apoptosis of senescent cells were examined.

Specifically, human umbilical cord vein derived vascular endothelial cells (HUVECs, Lonza) were cultured in a prescribed culture medium (EBM-2/EGM-2, Lonza). Less than 10 passages were defined as young and 15 passages or more were defined as aged. For young or aged HUVEC, 2DG, 3HB, and AIC were added to the culture solutions at the concentrations of 1 mM, 20 mM, and 200 μM, respectively, and the cells were harvested after 48 hours. The collected cells were evaluated for viability by fluorescence/absorbance measurements using ApoTox-Glo™ Triplex Assay kit (Promega). Dead cells were stained using AnnexinV (Becton & Dickinson (BD)), PI (Sigma-Aldrich), and Hoechst 33258 (Invitrogen), and the percentage of apoptosis-induced cells was quantified by FACS analysis.

Figure 9:
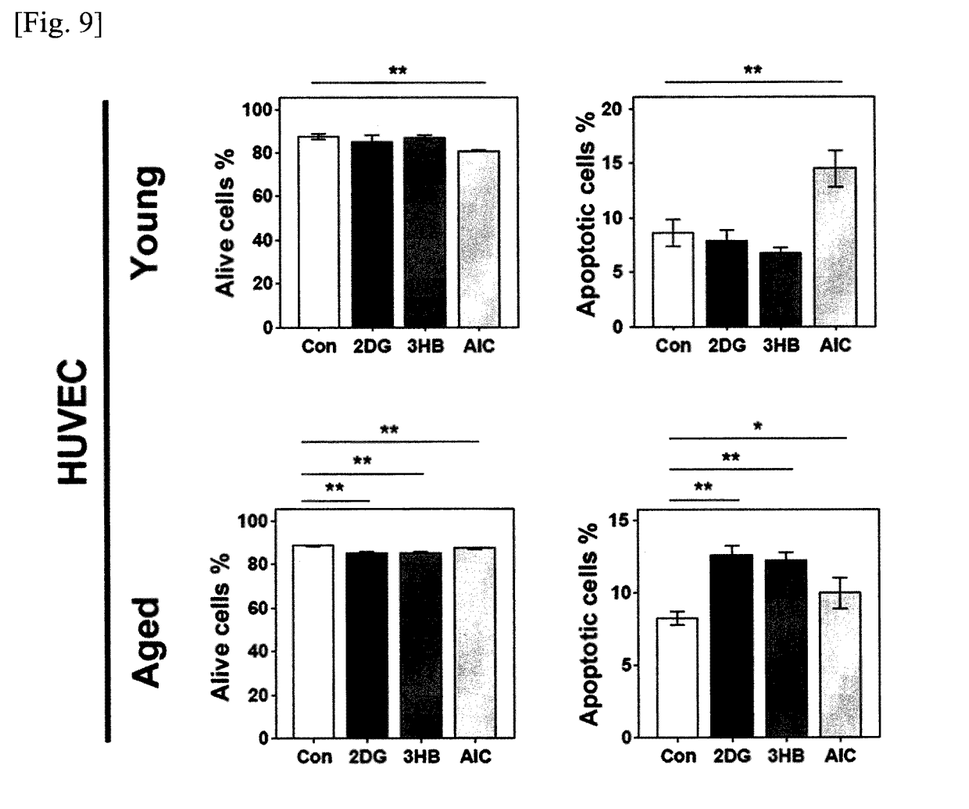
FIG. 9 is graphs showing cell viability and apoptosis induction when 2DG, 3HB, or AIC was added and when no reagent was added (Con) (Experimental Example 9) to young and aged HUVECs. The data are presented as mean±2 SE (n=3). *P<0.05, **P<0.01 (tested by Tukey's multiple comparison test after one-way ANOVA).

FIG. 9 is graphs showing cell viability and the percentage of apoptotic cells when 2DG, 3HB, or AIC was added and when no reagents were added (Con) to the young and the aged HUVECs. Relative to Con, 2DG and 3HB were shown to increase the apoptosis induction and to cause the decrease of the cell viability in an aged cell-selective manner. AIC also showed increased apoptosis induction and decreased cell viability, but they are not in an aged cell-selective manner as with seen in 2DG and 3HB, and rather, AIC exerted more potent effects in the young cells. The above results showed that 2DG and 3HB had an effect to eliminate senescent cells in an aged cell-selective manner, and suggested the possibility that SGLT2 inhibitor should eliminate senescent cells through the inhibition of glycolysis and the increase of the ketone body.

INDUSTRIAL APPLICABILITY

According to the present invention, senescent cells can be eliminated and a disease in which the disease state is expected to be improved by eliminating the senescent cells can be prevented and/or treated.

It will be apparent to those skilled in the art that the matters written herein in the singular form can be used in multiple unless the context clearly means otherwise.

It will also be apparent to those skilled in the art that any modifications can be made to the embodiments described herein without departing from the spirit of the invention, and such modifications are encompassed within the scope of the present invention.

This application claims priority of Patent Application No. 2016-167679 filed in Japan, the disclosure of which is incorporated herein by reference in its entirety.

The invention claimed is:

1. A method for reducing or eliminating senescent cells in a subject in need thereof, the method comprising administrating an effective amount of an SGLT2 inhibitor to the subject in need thereof to reduce or eliminate senescent cells.

* * * * *